United States Patent [19]
Ecanow

[11] 4,388,302
[45] Jun. 14, 1983

[54] COACERVATED IODINE

[75] Inventor: Charles S. Ecanow, Skokie, Ill.

[73] Assignee: NeoMed Corporation, Wilmette, Ill.

[21] Appl. No.: 258,050

[22] Filed: Apr. 28, 1981

[51] Int. Cl.³ .................... A01N 59/12; A61K 33/22
[52] U.S. Cl. .................................................. 424/150
[58] Field of Search ........................................ 424/150

[56]             References Cited
          U.S. PATENT DOCUMENTS
   4,088,597  5/1978  Morlock et al. .................... 424/150

OTHER PUBLICATIONS
Chemical Abstracts, vol. 83 (1975), Par. 127,344J.

Primary Examiner—Elbert L. Roberts
Attorney, Agent, or Firm—Edward A. Ptacek

[57]            ABSTRACT

A composition of matter and a method of preparing same are disclosed. In this disclosure this composition of matter is referred to as Coacervated Iodine. The disclosed method of manufacture combines urea with the lipoidal non polar aqueous phase of a two phase liquid aqueous system. Crystalline iodine is then dissolved in the lipoidal non polar aqueous phase. This procedure results in a powerful germicide which can be manufactured across a range of pH values extending from 3.4 to 7.5 without any loss of stability or germicidal activity.

8 Claims, No Drawings

COACERVATED IODINE

BACKGROUND

Iodine based preparations are commonly accepted as among the most effective of the available germicides. In addition, solution of iodine have been shown to possess fungicidal and viricidal properties. Iodine solutions appear to exhibit no selectivity against different strains of bacteria, all types being killed at approximately the same level of concentration and exposure time.

Numerous mixtures of iodine are now available. These include tincture of iodine, iodoform, iodine trichloride and the various iodophores. Of the available embodiments of iodine, the iodophores are in most common use and presently occupy the position of greatest interest.

The prior art teaches that crystalline iodine can be placed in solution through the use of surfactants such as polyvinyl-pyrrolidone, polyethoxyethanol derivatives and a variety of the quaternary ammonium compounds. These resulting mixtures of iodine and surface active agents are referred to in the scientific literature as iodophores.

Iodophore solutions are polar and micellar in character. Given that iodine is very insoluble in polar water, the problem of solubilization is partially solved in preparing iodophores by placing cystalline iodine in a micellar system. In effect, iodine is solubilized and carried in micellar aggregates which are formed through the use of surfactants. The micellar system acts as a reservoir which liberates iodine into the polar water and thence onto the surface to be treated.

It should be noted that iodophore mixtures exhibit maximum activity and stability in solutions, the pH of which must be within the range of 3.0 to 4.0. Solutions of iodine outside of this range show reduced stability and activity.

The use of surfactants to solubilize crystalline iodine only partially solves the problem of embodying non polar iodine in polar water. Investigation of the commercially available iodophores indicates that the inherent instability of iodine in polar water is not remedied in manufacture of these products. On analysis, iodophores are found to be complexes of indefinite components; ie. they are comprised of mixtures of all possible oxidative states of iodine. Further evidence of the instability of the iodine in iodophore preparations is found in the fact free iodine is eventually precipitated from such compositions. Moreover, when iodophores are evaporated to dryness on the skin surface for example, it is found that the individual component chemicals, ie. free iodine, free salts and surfactants are released onto the treated surface. Given the known irritant and toxic effects of free iodine and the reported carcinogenic potential of surfactants such as poly-vinylpyrrolidone, iodophore preparations would appear to have the possibility of exerting significant adverse effects.

(References: Ashwood-Smith, M. J. *Polyvinyl-pyrrolidone Solutions used in Plasma Expanders; Potential Carcinogens.* Lancet, 1, 1304, (1971).

Towers, R. P. *Lymph Node Changes due to Polyvinyl-Pyrrolidone*, Jour. of Clin. Pathology 10, 175–177, (1957).

OBJECTS

It is an object of this invention to disclose a method of manufacturing coacervated iodine. It is a further object to prepare coacervated iodine solutions that are germicidally active and pharmaceutically stable across a range of pH values extending from 3.4 to 7.5. Additional objects will appear self evident from the following disclosure.

THE INVENTION

This invention comprises a method of preparing coacervated iodine. This method of manufacture consists of the following steps:

(1) Forming a two phase aqueous liquid system; said system consists of and equilibrium water phase and a lipoidal non polar aqueous phase, herein also referred to as the coacervate phase.

(2) Adding an appropriate amount of dissolved urea to the liquid aqueous system of Step (1) above. The dissolved urea will partition between the two phases of the system.

(3) Separating the coacervate phase from the equilibrium water phase.

(4) Dissolving crystalline iodine in the coacervate phase.

Any of a number of surfactant agents can be used to manufacture the two phase aqueous liquid system. An alternate equally effective method of preparing this system substitutes acacia and gelatin complexes for surface active agents.

The unique physicochemical structure of this invention endows it with iodine vapor pressures that are significantly lower than those of known iodophores. Consequently, the claimed invention is believed to be significantly more stable than these latter preparations. As will become self evident, the claimed composition and its mode of manufacture have features in addition to structure which differentiate it from iodine based compositions now in use.

In iodophore preparation, the surfactant component is used to directly solubilize crystalline iodine and embody it in a micellar *polar* aqueous water medium. In contrast, in the claimed invention, the surfactant agent is used to prepare a two phase aqueous liquid system; the lipoidal *non polar* aqueous phase of this system is insoluble in polar water and dissolves crystalline iodine very readily. The coacervate phase used to manufacture the claimed composition will dissolve cystalline iodine even if the concentration of iodine is in the range of 10 to 20 percent.

In the present embodiment, the surface active agent binds and organizes the water of the composition; as such, it comprises an integral part of an aqueous matrix which is insoluble in normal polar bulk water. The resulting solvent system is completely different from that used in the formulation of bulk water micellar iodophore solutions.

It is important to emphasize that the *dissolution* of crystalline iodine by the coacervate phase of claimed invention contrasts with the *solubilization* of iodine that occurs in the manufacture of iodophores. In preparing iodophores, *solubilization produces a dispersion of iodine within the micelles of a solution* and thereby creates iodine complexes which are soluble in bulk water. In the claimed composition, *dissolution takes place and results in a dispersion of iodine (and/or iodophores) throughout the entire solution.* It follows from this, that a unique solution of dispersed free molecular iodine comprises this invention. Precipitation of free iodine or other components from the claimed preparation is virtually impossible.

It is evident from its mode of manufacture that the claimed invention enables the total reservoir of iodine to be continuously available to the surface being treated. Moreover, if the described composition is subjected to drying, it will evaporate to a gel. The resultant gel will maintain its structure indefinitely. The component ingredients will remain essentially unchanged. The germicidal, fungicidal and viricidal capability of the gel will continue indefinitely. In contrast, as described previously, when iodophore preparations are subjected to evaporation, they will dry to a powder with consequent liberation of free iodine, free salts and surfactant, and reduction in germicidal effectiveness.

Because of its coacervate structure, the interfacial tensions of the claimed invention are approximately ½ dyne per cm. By comparison, the interfacial tensions of commercially available iodophores are not less than 29 dynes per cm. It follows from these facts that the wettability of the claimed invention, ie. its ability to make and maintain contact with contiguous surfaces is clearly superior to that of known iodophores.

Unlike the iodophores which must be manufactured within a pH range of 3.0 to 4.0, the physicochemical structure of the claimed invention enable the preparation of embodiments which can range in pH from 3.4 to 7.5 without any compromise of its germicidal, fungicidal or viricidal activity. An obvious advantage of the proposed composition of matter is that it can be readily prepared to a pH identical to that of human or animal body fluids and tissues.

Because the previously described lipoidal non polar phase which is comprised largely of water is used in this invention to dissolve crystalline iodine, the proposed embodiment has all of the advantages of a water solvent; most notably it is non toxic and non irritating.

The prior art teaches that surface active agents can be directly substituted for alcohol to solubilize iodine. However, the prior art does not suggest that the coacervate phase of a two phase liquid aqueous system can be used to dissolve (as opposed to solubilize) crystalline iodine, nor that the use of the coacervate phase as disclosed in this invention will endow the proposed composition of matter with thermodynamic, vapor pressures, interfacial tensions and other features considered desireable in an effective germicide.

In the present invention urea is incorporated and constitutes an important component. Like iodine, urea has significant anti-bacterial, anti-fungal and anti-viral activity. However, urea has an additional property of direct significance to the proposed composition. It has the capability to alter the permeability of the walls of pathological organisms in such a way as to facilitate their destruction. Thus, as used in this invention, urea serves not only as a germicidal agent but also acts to facilitate the diffusion of iodine into disease producing organisms or aggregates thereof. As is evident, this action safely increases the known effectiveness of iodine as a germicide and antiseptic even further.

A number of surfactant agents such as benzylkonium chloride and dioctyl sulphosuccinate can be used to prepare the two phase liquid aqueous system from which the coacervate phase, necessary to this invention, is separated. If it is desired, the two phase system can also be made without the use of surface active agents. Other substances such as acacia and gelatin complexes can be substituted for the surfactant component.

EXAMPLES

In practicing this invention, the first step consists of preparing the two phase liquid aqueous system. Any of the surfactant agents referred to in descriptions that follow may be used to formulate the two phase system.

The claimed composition of matter may be embodied by means of any of the examples described below:

EXAMPLE 1

30 mls. of a 10% gelatin solution was added to 200 mls of a 5% benzylkonium chloride solution containing 5% weight to volume of urea dissolved in distilled water. Sufficient 0.1% sodium hydroxide solution was added until a pH of 9.5 was reached. The resultant solution was then diluted to 1500 mls. with distilled water. The solution was then placed in a flat bottom glass flask, sealed and mixed vigorously for 15 minutes by vortex mixer. On completion of this step, the flask and its contents were stored undisturbed for 24 hours at 37 degrees C. At the end of this period, the solution had divided into two distinct layers. The lower layer comprised the lipid, non polar aqeous liquid phase, herein also referred to as the coacervate phase. The upper layer comprised the equilibrium water phase. The two layers were then separated by means of a separatory funnel and the equilibrium water phase discarded. To 100 mls. of the coacervate phase 1 gram of crystalline iodine was added. The solution was stirred vigorously by vortex mixer at room temperature for 30 minutes. By the end of this time, the iodine had completely dissolved. The preparation was then titrated to a pH of 7.5 by the drop by drop addition of dilute hydrochloric acid. The preparation was then ready for either immediate use or storage in appropriate glass or plastic containers. Storage took place at 20 degrees C.

EXAMPLE 2

10% weight to volume of sodium di (2 ethyexyl) sulfosuccinate was dispersed in 1000 mls. of distilled water which contained 3% weight to volume of urea dissolved in distilled water. A solution of 1.8% sodium chloride was added to this mixture until oil like droplets began to form and settle to the bottom of the flask. This event marked the forming of the two phase liquid aqeous system. The process of droplet formation and settling was allowed to proceed until no further settling and no change in the volumes of the two phases was observed. The next step consisted of separating the two phases by means of a separatory funnel and discarding the equilibrium water phase. To 100 mls of the coacervate phase, 1 gram of crystalline iodine was added and using a vortex mixer, the solution was thoroughly mixed for 30 minutes at room temperature. The iodine was observed to have been completely dissolved by the end of the 30 minute period. The solution was then titrated to a pH of 6.5 by the addition of the necessary amount of dilute hydrochloric acid. The preparation now completed was then stored in glass containers at room temperature.

EXAMPLE 3

A 6% solution, weight to volume of acacia was added to a 5% weight to volume solution of gelatin. Dilute hydrochloric acid was then added drop by drop until a pH of 4 was reached. The solution was next mixed vigorously at room temperature by vortex mixer for two minutes. The solution was then stored undisturbed at room temperature for twelve hours. At the end of the twelve hour period, the two phase aqueous liquid system had formed; ie. the solution had separated into two distinct layers. The bottom layer constituted the coacervate phase; the upper layer comprised the equilibrium phase which was discarded after separation of the phases by means of a separatory funnel. To 100 mls. of the coacervate phase 1 gram of crystalline iodine was added. Using a vortex mixer, the solution was mixed thoroughly at room temperature for 30 minutes. The iodine had completely dissolved by the end of this period. The composition was then stored in appropriate glass containers at room temperature.

EXAMPLE 4

The procedure of Example 4 followed that of Example 3 except that 2 grams of crystalline iodine was added to 100 mls of the coacervate phase.

EXAMPLE 5

3 mls of a 10% gelatin solution was added to 2 mls. of an 8% benzylkonium chloride solution containing 5% weight to volume of urea dissolved in distilled water. Sufficient 0.1% sodium hydroxide solution was added until a pH of 9.25 was reached. The resultant solution was then diluted to 1500 mls. with distilled water. The rest of the procedure followed Example 1 except that 2 grams of crystalline iodine was added to 100 mls. of the coacervate phase.

EXAMPLE 6

10% weight to volume of sodium di (2 ethylexyl) sulfosuccinate was dispersed in 100 mls. of distilled water which contains 3% weight to volume of dissolved urea. A solution of 3% sodium chloride was added drop by drop to this mixture until oil like droplets began to form and settle to the bottom of the flask. The rest of the procedure followed that of Example 2 except that a sufficient amount of polyvinyl-pyrrolidone powder was added to the coacervate phase so as to result in a finished product contained 1% iodine.

EXAMPLE 7

The procedure of Example 7 followed that of Example 1 except that 2% weight to volume of urea dissolved in distilled water was added to the coacervate phase after it had been separated from its equilibrium water phase.

The pH of any coacervated iodine preparation can be adjusted to any value from 3.4 to 7.5 by adding the appropriate amount of sodium hydroxide or dilute hydrochloric acid and titrating to the desired pH.

The examples of embodiments of this invention given previously contain many specifications. These should not be construed as limitations on the scope of the invention but rather as exemplifications of preferred embodiments. Many other desireable variations are possible. Accordingly, the scope of this invention should not be determined by the described embodiments but by the appended claims and their legal equivalents.

USE OF COACERVATED IODINE

Regardless of which of the described methods by means of which coacervated iodine may be manufactured, the claimed composition is equally effective as a germicidal, fungicidal and viricidal agent. Under appropriate conditions, any of the described embodiments of this invention can be used for space disinfection.

Absorption of the claimed composition of matter onto surfaces such as bandages does not affect its antiseptic effectiveness.

Using standarized, well known manufacturing processes coacervated iodine can be prepared in all of the regular dosage forms; ie. solutions, ointments, foams, gels, suspensions, emulsions and detergents. Through microencapsulation procedures, powdered forms of coacervated iodine can be prepared. In this form, coacervated iodine may be used to dust open wounds or abrasions with germicidal effect. While coacervated iodine can be used to disinfect or sterilize most mucous membrane surfaces, it should not be introduced into the eye.

EXPERIMENTS

The following are descriptions and results of experiments designed to test the germicidal effectiveness and stability of the claimed invention.

EXPERIMENT 1

This experiment was conducted to determine the length of time that was required to kill selected test bacteria in full strength, half strength and quarter strength solutions of coacervated iodine prepared according to Example 1. The bacteria used included the following test organisms:
*Streptococcus pyogenes*
*Staphylococcus aureus*
*Proteus vulgaris*
*Klebsiella pneumoniae*
*Shigella sonnei*
*Staphylococcus epidermis*
*Escheria coli*
*Candida albicans*
*Salmonella typhosa*
*Pseudomonas aeruginosa*

One half ml. of each organism given above, was used in this test. The temperature at which the experiment was conducted was 37 degrees C. The concentrations of coacervated iodine used were as follows:
1% solution full strength
1% solution half strength
1% solution quarter strength Each bacterial sample in the amount stated above was introduced into a test tube containing 5 ml. of the claimed composition. After 0.5 minutes, the mixture was sub cultured to determine the presence of viable bacteria. Further subculturing was done at 1 minute, 5 minute, and 10 minute intervals.

All bacteria used in this experiment were killed within 30 seconds in each of the concentrations of coacervated iodine given above.

EXPERIMENT 2

This experiment was conducted to determine the influence of organic matter on the germicidal activity of the claimed invention when prepared as per Example 2.

This experiment used sterile rabbit blood in a concentration of 10% as the organic contaminant. The temperature at which the test was conducted was 37 degrees C. Twenty four hour cultures of the following microorganisms were used as the test bacteria:
*Streptococcus pyogenes*
*Staphylococcus aureus*
*Proteus vulgaris*
*Klebsiella pneumoniae*
*Shigella sonnei*

*Staphylococcus epidermis*
*Escheria coli*
*Candida albicans*
*Salmonella typhosa*
*Pseudomonas aeruginosa*

Sub culturing was done at 15 seconds, 30 seconds, 45 seconds, 1, 2, and 5 minutes. To obtain the experimental mixture of organic material, 1 ml. of a mixture of equal parts of whole rabbit blood and broth culture of each test organism was added to 5 mls of a 1% solution of coacervated iodine. The control phase of this experiment consisted of tests of coacervated iodine against the bacteria described above, except that tests were done in the absence of organic material. Sub culturing and other procedures were identical in both the control and experimental tests.

The following results were obtained from this experiment. Using sterility end point as the criterion of germicidal activity, it was found that in the absence of organic material, germicidal activity against *Staphylococcus aureus* occurred within 45 seconds. Germicidal activity was observed within 30 seconds in all other bacteria used in this test. In the presence of 10% organic material, using the criterion given above, germicidal activity was again observed to occur within 45 seconds against *Staphylococcus aureus* and within 30 seconds against all other organisms tested. These results demonstrate that the germicidal activity of coacervated iodine is not affected by the presence of a 10% concentration of organic matter, ie. rabbit blood.

EXPERIMENT 3

This test was conducted to determine the stability of coacervated iodine and the availability of the embodied iodine throughout a 59 day period when stored at a temperature of 6 degrees C. following manufacture as per Example 1.

This experiment utilized full strength, half strength, and quarter strength solutions of 1% coacervated iodine. All analyses were performed at room temperature.

Thirty samples of 50 cc coacervated iodine consisting of 10 at full strength, ie. 1%; 10 at half strength and 10 at quarter strength were placed in a refrigerator at 6 degrees C. One sample was randomly selected and removed for analysis every two days. Each sample studied was allowed to stand until it reached room temperature (25 degrees C.) before analysis for available iodine was undertaken. On reaching room temperature, a 25 ml. aliquot was taken from the sample. The percentage of available iodine was determined by titrating a 25 cc sample of coacervated iodine as described above with 0.1 N Sodium thiosulphate.

| | | Test Results | | |
|---|---|---|---|---|
| Day | 1 | Sample | 1 (Full strength) | Available Iodine 1.01 |
| | 3 | | 2 (½ strength) | 1.01 |
| | 5 | | 3 (¼ strength) | 1.01 |
| | 7 | | 4 (½ strength) | 1.01 |
| | 9 | | 5 (Full strength) | 1.01 |
| | 11 | | 6 (Full strength) | 1.01 |
| | 13 | | 7 (¼ strength) | 1.01 |
| | 15 | | 8 (¼ strength) | 1.01 |
| | 17 | | 9 (Full strength) | 1.01 |
| | 19 | | 10 (¼ strength) | 1.01 |
| | 21 | | 11 (¼ strength) | 1.01 |
| | 23 | | 12 (¼ strength) | 1.01 |
| | 25 | | 13 (¼ strength) | 1.01 |
| | 27 | | 14 (Full strength) | 1.01 |
| | 29 | | 15 (¼ strength) | 1.01 |
| | 31 | | 16 (Full strength) | 1.01 |
| | 33 | | 17 (½ strength) | 1.01 |
| | 35 | | 18 (½ strength) | 1.01 |
| | 37 | | 19 (Full strength) | 1.01 |
| | 39 | | 20 (¼ strength) | 1.01 |
| | 41 | | 21 (¼ strength) | 1.01 |
| | 43 | | 22 (Full strength) | 1.01 |
| | 45 | | 23 (Full strength) | 1.01 |
| | 47 | | 24 (½ strength) | 1.01 |
| | 49 | | 25 (½ strength) | 1.01 |
| | 51 | | 26 (½ strength) | 1.01 |
| | 53 | | 27 (½ strength) | 1.01 |
| | 55 | | 28 (½ strength) | 1.00 |
| | 57 | | 29 (½ strength) | 1.00 |
| | 59 | | 30 (Full strength) | 1.00 |

EXPERIMENT 4

This test was conducted to determine the stability of coacervated iodine and the availablity of the embodied iodine throughout a 59 day period following manufactured as per Example 1 and stored at a temperature of 52 degrees C.

This experiment was based upon full strength, half strength and quarter strength solutions of coacervated iodine. All analyses of stability and availability were performed at room temperature.

Thirty samples of 50 cc coacervated iodine consisting of 10 at full strength, ie. 1%; 10 at half strength and 10 at quarter strength were placed in a laboratory oven preheated to a temperature of 52 degrees C. All samples remained at this temperature until they were drawn for analysis. One sample was randomly selected and removed for analysis every two days. Each sample was allowed to stand undisturbed until it reached room temperature (25 degrees C.) before stability and availability tests were performed. On reaching room temperature a 25 ml. aliquot was taken from the sample for study. The percentage of available iodine was determined by titrating the 25 cc sample of coacervated iodine with 0.1 N Sodium thiosulphate.

| | | Test Results | | |
|---|---|---|---|---|
| Day | 1 | Sample | 1 (¼ strength) | Available Iodine 1.01 |
| | 3 | | 2 (Full strength) | 1.01 |
| | 5 | | 3 (¼ strength) | 1.01 |
| | 5 | | 3 (½ strength) | 1.01 |
| | 7 | | 4 (¼ strength) | 1.01 |
| | 9 | | 5 (¼ strength) | 1.01 |
| | 11 | | 6 (¼ strength) | 1.01 |
| | 13 | | 7 (Full strength) | 1.01 |
| | 15 | | 8 (¼ strength) | 1.01 |
| | 17 | | 9 (¼ strength) | 1.01 |
| | 19 | | 10 (Full strength) | 1.01 |
| | 21 | | 11 (Full strength) | 1.01 |
| | 23 | | 12 (¼ strength) | 1.01 |
| | 25 | | 13 (Full strength) | 1.01 |
| | 27 | | 14 (¼ strength) | 1.01 |
| | 29 | | 15 (½ strength) | 1.01 |
| | 31 | | 16 (¼ strength) | 1.01 |
| | 33 | | 17 (¼ strength) | 1.01 |
| | 35 | | 18 (Full strength) | 1.01 |
| | 37 | | 19 (½ strength) | 1.01 |
| | 39 | | 20 (Full strength) | 1.01 |
| | 41 | | 21 (½ strength) | 1.01 |
| | 43 | | 22 (Full strength) | 1.01 |
| | 45 | | 23 (½ strength) | 1.01 |
| | 47 | | 24 (½ strength) | 1.00 |
| | 49 | | 25 (½ strength) | 1.00 |
| | 51 | | 26 (Full strength) | 1.00 |
| | 53 | | 27 (¼ strength) | 1.00 |
| | 55 | | 28 (Full strength) | 1.00 |
| | 57 | | 29 (¼ strength) | 1.00 |

-continued

| | Test Results | |
|---|---|---|
| 59 | 30 (½ strength) | 1.00 |

EXPERIMENT 5

This test was conducted to determine the potential of coacervated iodine to cause skin irritation, scar formation and edema. 1% coacervated iodine solution prepared according to Example 1 was used as the test solution.

Six smooth haired white guinea pigs were the test animals. The group consisted of three male and three female animals. One and one half inch square patches of skin on the right and left side of each animal were shaved to remove all hair. The skin on the right side patch was abraded in a cross hatch pattern using a sterile hypodermic needle. The abrading extended into the superficial layer of the skin. The skin patch on the left side of the animal was not disturbed. A 0.5 ml sample of the coacervated iodine solution was applied to both the right and left side skin patches by means of a cotton applicator. Patches of sterile surgical gauze, two layers thick were used to cover the treated areas. The gauze patch was covered with non reactive adhesive tape. The skin patches were examined 24 and 72 hours after the coacervated iodine solution had been applied. Using the scale given in the Federal Hazardous Substances Act, the patches of skin were examined for reaction and rated.

| | | Results Ratings for animal no. | | | | | | Total |
|---|---|---|---|---|---|---|---|---|
| Reaction | Time (hours) | 1 | 2 | 3 | 4 | 5 | 6 | score |
| Erythema and scar formation | | | | | | | | |
| Intact | 24 | 0 | 0 | 0 | 0 | 0 | 0 | 0 |
| Abraded | 24 | 0 | 0 | 0 | 0 | 0 | 0 | 0 |
| Intact | 72 | 0 | 0 | 0 | 0 | 0 | 0 | 0 |
| Abraded | 72 | 0 | 1 | 0 | 0 | 0 | 0 | 1 |
| Edema | | | | | | | | |
| Intact | 24 | 0 | 0 | 0 | 0 | 0 | 0 | 0 |
| Abraded | 24 | 0 | 1 | 0 | 0 | 0 | 0 | 1 |
| Intact | 72 | 0 | 0 | 0 | 0 | 0 | 0 | 0 |
| Abraded | 72 | 0 | 0 | 0 | 0 | 0 | 0 | 0 |

Note
(1) Animals 1, 3, 5, were male guinea pigs; animals 2, 4, 6 were female guinea pigs.
(2) A rating of 0 indicates no reaction. A rating of 1 indicates very slight reaction; thus, animal number 2 demonstrated slight erythema and slight edema. Neither reaction was evident at the 72 hour examination.

Using standardized, well known manufacturing processes, Coacervated Iodine can be prepared in all of the regular dosage forms; ie. solutions, ointments, gels, suspensions, foams and emulsions. Through microencapsulation procedures, powdered forms of Coacervated Iodine can be prepared. In this form, Coacervated Iodine may be used to dust open wounds or abrasions with germicidal effect. While Coacervated Iodine should not be introduced into the eye, in appropriate dosage form, Coacervated Iodine can be used to disinfect or sterilize most mucous membrane surfaces.

The examples of embodiments of this invention given previously, contain many specificities. These should not be construed as limitations on the scope of the invention but rather as exemplifications of preferred embodiments. Many other desireable variations are possible. Accordingly, the scope of this invention should not be determined by the described embodiments but by the appended claims and their legal equivalents.

SUMMARY

This invention relates to a composition of matter herein referred to as Coacervated Iodine and to a method of making this composition. The method of manufacture makes use of (1) the lipoidal non polar aqueous phase of a two phase aqueous liquid system to dissolve crystalline iodine or iodine based preparations such as iodophores and (2) incorporates urea in such manner as to enhance the known germicidal, fungicidal and viricidal properties of iodine. The product that results from this mode of manufacture is unusually stable and highly effective against a broad array of pathogenic micro-orgnisms. The claimed invention is pharmaceutically stable and germicidally active across a range of pH values from 3.4 to 7.5. To achieve maximal activity and stability, the iodine based preparations now in most common use, ie. the iodophores must be manufactured to a pH of 3.0 to 4.0.

What I claim and desire to protect by Letters Patent:

1. A method of preparing coacervated iodine which comprises the steps of:
    (a) preparing a two phase aqueous liquid system wherein one phase is a lipoidal non polar aqueous phase, herein also referred to as the coacervate phase, and the second phase is an equilibrium water phase;
    (b) adding dissolved urea to the two phase aqueous liquid system of step (a) above;
    (c) separating the coacervate phase from the equilibrium water phase;
    (d) dissolving crystalline iodine in the coacervate phase which now contains a quantity of dissolved urea.

2. The method of claim 1 wherein dissolved urea is added to the coacervate phase after that phase is separated from the equilibrium water phase.

3. The method of claim 1 wherein the two phase aqueous liquid system is prepared by using a surface active agent.

4. The method of claim 1 wherein the two phase aqueous liquid system is prepared by using an agent selected from the group consisting of acacia and gelatin complexes.

5. The method of claim 1 wherein the two phase aqueous liquid system is prepared by using from 1 to 10% of a surfactant.

6. The method of claim 1 wherein the coacervate phase which contains urea and in which crystalline iodine has been dissolved can range in pH values from 3.4 to 7.5.

7. The method of claim 3 wherein the surfactant used is selected from the group consisting of benzylkonium chloride and dioctyl sulphosuccinate.

8. A composition of matter useful as a germicide and antiseptic, prepared according to the method of claim 1.

* * * * *